US009129099B1

(12) United States Patent  (10) Patent No.: US 9,129,099 B1
Paruchuri  (45) Date of Patent: Sep. 8, 2015

(54) PORTABLE HEALTH RECORD SYSTEM AND METHOD

(76) Inventor: Vamsi Krishna Paruchuri, Conway, AR (US)

( * ) Notice: Subject to any disclaimer, the term of this patent is extended or adjusted under 35 U.S.C. 154(b) by 180 days.

(21) Appl. No.: 13/211,911

(22) Filed: Aug. 17, 2011

Related U.S. Application Data

(60) Provisional application No. 61/374,292, filed on Aug. 17, 2010.

(51) Int. Cl.
*G06F 21/00* (2013.01)
*G06F 21/30* (2013.01)
*G06F 21/62* (2013.01)

(52) U.S. Cl.
CPC ............ *G06F 21/30* (2013.01); *G06F 21/6245* (2013.01)

(58) Field of Classification Search
CPC ... G06F 19/323; G06F 19/3418; G06F 21/30; G06F 21/6245
USPC .............................................. 713/156; 705/3
See application file for complete search history.

(56) References Cited

U.S. PATENT DOCUMENTS

| | | | | |
|---|---|---|---|---|
| 5,931,917 | A * | 8/1999 | Nguyen et al. | 709/250 |
| 2005/0216313 | A1* | 9/2005 | Claud et al. | 705/3 |
| 2006/0076420 | A1* | 4/2006 | Prevost et al. | 235/492 |
| 2010/0228968 | A1* | 9/2010 | Wason et al. | 713/156 |

OTHER PUBLICATIONS

Marupally, P. R., Paruchuri, V., & Chellappan, S. (Aug. 2009). Privacy Preserving Portable Health Record (P3HR). In Network-Based Information Systems, 2009. NBIS'09. International Conference on (pp. 310-315). IEEE.*
Chou, Wesley. "Inside SSL: the secure sockets layer protocol." IT professional 4.4 (2002): 47-52.*
Chan, Alvin Ts. "WWW+ smart card: towards a mobile health care management system." International journal of medical informatics 57.2 (2000): 127-137.*
Gupta, V., Gupta, S., Chang, S., & Stebila, D. (Sep. 2002). Performance analysis of elliptic curve cryptography for SSL. In Proceedings of the 1st ACM workshop on Wireless security (pp. 87-94). ACM.*
Huawei, Z., & Ruixia, L. (May 2009). A scheme to improve security of SSL. In Circuits, Communications and Systems, 2009. PACCS'09. Pacific-Asia Conference on (pp. 401-404). IEEE.*
Steele, R., & Min, K. (Apr. 2010). HealthPass: fine-grained access control to portable personal health records. In Advanced Information Networking and Applications (AINA), 2010 24th IEEE International Conference on (pp. 1012-1019). IEEE.*

* cited by examiner

*Primary Examiner* — Syed Zaidi

(57) ABSTRACT

A Privacy Preserving Portable Health Record ($P^3HR$) based on Smart Enterprise Guardian (SEG) that incorporates smart card security and advanced flash storage encryption technology gives a patient the flexibility of using the services of a variety of generally unrelated healthcare practitioners and providers with control over their health records and the ability to provide comprehensive access to the patient's health records as would occur in a centralized clinic setting to in effect create a virtual medical clinic. The security architecture of the $P^3HR$ serves a group of medical patients, healthcare practitioners, and other associated providers such as hospitals and insurance providers. The system provides for continuously updated healthcare history of patients in a remote update server and on portable access devices, which are carried by patients.

20 Claims, 2 Drawing Sheets

PORTABLE HEALTH RECORD SYSTEM AND METHOD

CROSS-REFERENCE TO RELATED APPLICATIONS

This application claims the benefit of U.S. provisional patent application No. 61/374,292, filed on Aug. 17, 2010, and entitled "Privacy Preserving Portable Health Record." Such application is hereby incorporated by reference in its entirety.

STATEMENT REGARDING FEDERALLY SPONSORED RESEARCH OR DEVELOPMENT

Not applicable.

BACKGROUND OF THE INVENTION

As concerns continue to mount over rising health care costs, many believe that patients must be more engaged in their own health care, assume an active role in the management of their care, and take greater responsibility for its cost and quality. Personal health records (PHRs) could support patient-self management and engagement, and electronic versions of PHRs would facilitate access to comprehensive health information as well as improve patient/physician communications. Moreover, patients are interested in having more information about their own health care.

There are primarily three categories of PHR services available today, those that are Internet-based, portable device-based, and token-based. Internet-based PHR services begin with a registration process that involves the user choosing a username and password. Through a web interface, users then complete information about their (or a family member's) health that is stored in a secure document maintained by the PHR company. Users can access that information (and/or authorize access by others such as emergency contacts, physicians, or emergency room departments) by logging-in and providing their password.

Portable device-based services comprise a second category of available PHR services. Several companies featured various types of digital memory portable devices containing one's health information that could be carried around on lanyards, key chains, watches, bracelets, pens, laser pointers, or on credit-card wallet CDs. The information is launched by "plugging" that device into a computer in a physician's office or an emergency room.

Token-based PHR services comprise a third category, typically implemented as smart cards. Despite interoperability concerns, smart cards and the like can be an economical way of exchanging medical information across organizations.

In the field of Internet-based PHR services, patients today have many choices when selecting a PHR system that meets their needs. Their healthcare providers, employers, or insurers may offer them a PHR at little or no cost. They can also select from a growing number of PHR vendors who offer either a software application or online service. An example of an open source PHR is the iHealth Record.

The iHealth Record was released in May 2005 by Medem. It was a joint venture of the American Medical Association (AMA) and other healthcare organizations. Key features include online consultations for patients paid for by health plans; email capabilities between doctors and their patients; and the inclusion of current medical conditions, medications, past surgeries, and allergies, as well as end-of-life directives.

It is generally considered insecure to put this type of information out on the Internet for everyone to see—and unfortunately that is the result of using the existing online PHR applications. They are often disguised as services that provide free storage for medical information, but privacy is not assured. In addition, the patient may as a result be the subject of spam emails or postal "junk" mail that is undesired.

Turning to portable device-based services, the E-Health KEY is a secure and portable PHR using universal serial bus (USB) flash drive technology. The E-Health KEY detects whether it is plugged into the "home" computer or into an unknown computer. If plugged into an unknown computer, the E-Health KEY assumes that it is being inserted into a computer of an emergency room (ER) or an ambulance. The application will immediately pull up and present only the critical medical information such as medical conditions, medications, allergies, etc., that the patient/member has previously authorized for broader disclosure.

The first time the E-Health KEY is connected to the home computer, its application installs a small interactive utility program that facilitates interaction with the Medic Alert membership database via the Internet, and offers users additional utilities as well.

It is important to note that the computers used by most medical and emergency personnel are firewalled or require administrative privileges in order to install any software. This means that in an emergency, products that require installation of proprietary software are not usable by those services, which may well slow down access to patients vital information by emergency personnel. Medic Alert also does not support any security measures such as encryption, password protection, or access control mechanisms, thereby leaving open the possibility of comprise of the stored data in the case that the device containing the data is lost or stolen.

Finally, with respect to token-based PHR services such as smart card-based PHR services, Mount Sinai Medical Center in New York City is working closely with Siemens to develop the Patient Health Card solution and began deploying smart cards as part of its 10-institution pilot program. The project was designed to demonstrate the benefits and value of smart cards locally and across organizations as a way to exchange medical information among disparate institutions. The network created with smart cards will allow facilities with varying information systems to share and exchange medical data in a secure and patient-controlled manner. The Health Smart Network will initially link nine hospitals and one community clinic using smart cards. The intent is to expand the network throughout the New York metropolitan area. The ambitious pilot program underway at Mount Sinai, where officials expect to roll out 100,000 cards, could change how doctors and hospitals view smart card technology.

In an open environment, where various entities from different administrative domains (e.g., hospitals, pharmacies, and insurance companies) exchange data, support of electronic data interchange (EDI) is mandatory. However, there are only some particular specifications that could be used in the medical sector, such as a physician letter, hospital-to-hospital documentation, etc. Many of these are intended for other business sectors. As a result, costly converters are needed, which poses problems for true interoperability. To make things worse, there are some basic data sets like electronic patient records that have yet to be standardized. Furthermore, the organization must decide on the nature of the information on a health care smart card. It has been proposed that a smart card merely serve as an access control device in drawing information from an on-line database, but this does not take full advantage of the capabilities of a smart card, and also raises additional transmission and privacy concerns.

The underlying technology to support smart card functionality has been in development for some time. A smart card is a device that includes an embedded integrated circuit chip (ICC) that can be either a secure microcontroller or equivalent intelligence with internal memory or a memory chip alone. The card connects to a reader with direct physical contact or with a remote contactless radio frequency interface. With an embedded microcontroller, smart cards have the unique ability to store large amounts of data, carry out their own on-card functions (e.g., encryption and mutual authentication) and interact intelligently with a smart card reader. Smart card technology today generally conforms to international standards (ISO/IEC 7816 and ISO/IEC 14443) and is available in a variety of form factors, including plastic cards, fobs, subscriber identification modules (SIMs) used in GSM mobile phones, and USB-based tokens. Smart cards are used in many applications worldwide, including secure identity applications (such as employee ID badges, citizen ID documents, electronic passports, driver's licenses, and online authentication devices); healthcare applications (such as citizen health ID cards, physician ID cards, and portable medical records cards); payment applications (such as contact and contactless credit/debit cards, and transit payment cards); and telecommunications applications (such as GSM SIMs and pay telephone payment cards).

One particular smart card technology that was recently developed to provide enhanced security features is Smart Enterprise Guardian (SEG), a product developed by Gemalto NV. SEG is a unique USB device based on industry standards that secures identity credentials and sensitive files with proven smart card technology incorporated with a flash drive storage mechanism in a single unit. It protects up to 2 GB of data on a USB drive and supports strong authentication, digital signature, and file encryption. It enables enterprises of all sizes to protect network access and confidential information; enhance productivity with easy to use security services and simple administration; make business transactions more efficient and safe; and optimize return on investment with a highly interoperable solution that leverages existing information technology infrastructure. This device is one of the first personal portable security devices (PPSD) that offers secure portable memory with advanced encryption standard (AES) 256-bit hardware-based encryption and strong authentication using public key infrastructure (PKI) services.

It may be seen from the above discussion that as the health care industry shifts more toward a more consumer-oriented focus, the desire for patients to have greater access to their PHRs grows. Personal health records offer many potential benefits, including quick access to information that could be a lifesaver in an emergency situation. But the technology is still evolving, and many challenges are yet to be worked out. Some of the chief challenges of the current PHR systems include interoperability, security requirements, privacy, and environmental barriers.

Currently, interoperability is limited in a number of ways. First, most PHR systems in use today are integrated with one provider's electronic health record (EHR) system, in effect serving as a portal view into the EHR. This provides tight integration between what the patient sees and what the provider sees. However, if EHR systems are not interoperable, the content would be primarily limited to what is stored in that provider's EHR.

Security is a continuing problem because, particularly with an Internet-based PHR system, multiple individuals, such as family members and caregivers, may view and contribute patient information. The security requirements of ensuring authentication and access control in this context thus represents a major challenge.

The privacy of health information stored on a stand-alone web site may not be as secure as data stored by a health care system, which must comply with privacy rules mandated by the federal government's Health Insurance Portability and Accountability Act (HIPAA), as well as its implementing regulations.

Finally, there are multiple environmental barriers to PHR implementation. Health information on each patient now generally resides in multiple locations. As a result, integrated PHRs must reach across organizational boundaries to interface with multiple EHR systems. The lack of ubiquitous EHR usage currently presents the greatest environmental barrier to such integrated PHR adoption. A related problem is that EHRs must not only exist in individual offices and hospitals but must also be able to communicate with PHRs. Economic and market forces are obstacles to PHR (and EHR) adoption. Many vendors offering stand-alone PHRs have not been financially successful; numerous products and companies are no longer in existence.

References mentioned in this background section are not admitted to be prior art with respect to the present invention.

BRIEF SUMMARY OF THE INVENTION

In certain of its various embodiments, the present invention is directed to a Privacy Preserving Portable Health Record ($P^3HR$) based on Smart Enterprise Guardian (SEG) technology or similar technologies that incorporate smart card security and advanced flash storage encryption technology. The $P^3HR$ gives a patient the flexibility of using the services of a variety of generally unrelated healthcare practitioners and providers with control over their health records and the ability to provide comprehensive access to the patient's health records as would occur in a centralized clinic setting to in effect create a virtual medical clinic.

One of the salient features of the preferred embodiment of the invention is its interoperability. Hospitals and other healthcare provider organizations typically have many different computer systems used for everything from billing records to patient tracking. All of these systems should communicate with each other (or "interface") when they receive new information but not all do so. Health Level Seven (HL7) specifies a number of flexible standards, guidelines, and methodologies by which various healthcare systems can communicate with each other. Such guidelines or data standards are a set of rules that allow information to be shared and processed in a uniform and consistent manner.

These data standards are meant to allow healthcare organizations to easily share clinical information. Theoretically, this ability to exchange information should help to minimize the tendency for medical care to be geographically isolated and highly variable. The preferred embodiment uses HL7 to ensure interoperability with various hospitals and other healthcare provider organizations. Profiling is also used as a way to enforce interoperability. The preferred embodiment ensures both the system-level interoperability and the spatial interoperability of health data across all public health authorities as well as between health care providers such as hospitals, clinics, physicians, and emergency responders.

The security architecture of the $P^3HR$ in a preferred embodiment serves a group of medical patients, healthcare practitioners (physicians, dentists, nurses, pharmacies, etc.), and other associated parties such as hospitals and insurance providers. Such system provides for continuously updated healthcare history of patients in a remote update server and on portable access devices, which are carried on patients.

In a first aspect, the present invention is directed to a portable health record system, comprising an update server operated by a provider to provide access to and updates to a provider health record, wherein the provider health record provides data regarding at least one patient; a client server operated by a patient in communication with the update server via a network; a smart card in communication with the client server, wherein the smart card comprises non-volatile memory comprising a patient health record comprising data regarding the patient; and a portable health record manager application operable to communicate with the update server over the network to transfer data regarding the patient between the provider health record and the patient health record; and a backup server in communication with the update server and the client server and operable to store a backup copy of the patient health record.

In a second aspect, the invention is directed to a method of authenticating a provider and patient using a portable health record system, the method comprising the steps of sending a patient hello message over a network from the patient, at a client server in communication with a smart card comprising non-volatile memory storing a patient health record, to the provider, at a remote update server providing access to a provider health record, wherein the patient hello message comprises a pseudorandom number; sending a provider hello message over the network from the provider to the patient, wherein the provider hello message comprises a pseudorandom number; computing at a portable health record manager application operating on the client computer and stored on the smart card a premaster secret using the patient hello message pseudorandom number and the provider hello message pseudorandom number; sending a patient key exchange message from the patient to the provider, wherein the patient key exchange message comprises the premaster secret; computing a master secret at the provider utilizing the pre-master secret; sending a patient finish message from the patient to the provider comprising a has of the previous messages exchanged by the provider and patient; sending a provider finish message from the provider to the patient; and sending at least one encrypted message between the provider and patient, wherein the encrypted message may be decrypted using the master secret.

These and other features, objects and advantages of the present invention will become better understood from a consideration of the following detailed description of the preferred embodiments and appended claims in conjunction with the drawings as described following:

DETAILED DESCRIPTION OF THE PREFERRED EMBODIMENT(S)

Figure 1:
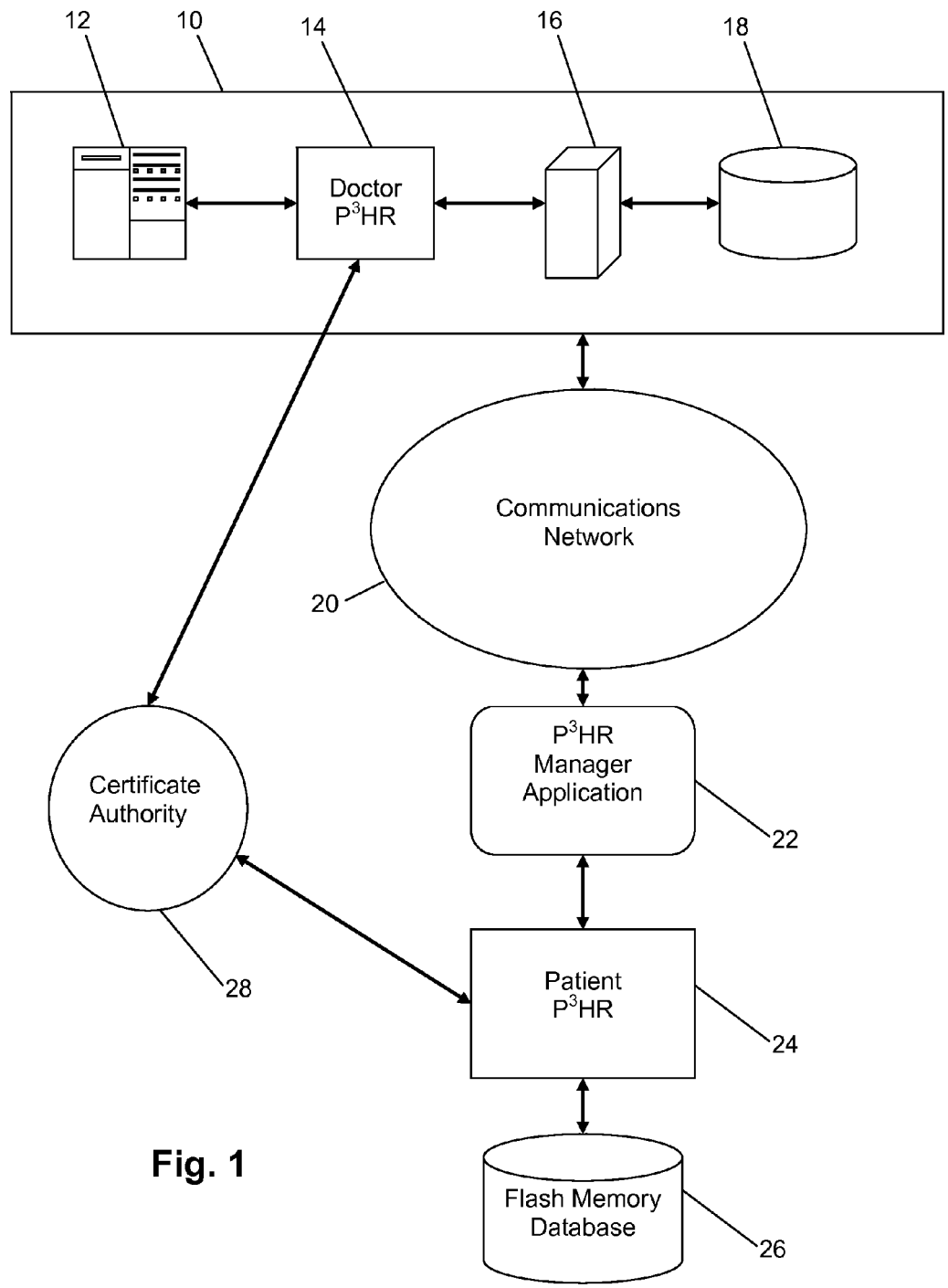
FIG. 1 is a functional schematic depicting the architecture of a P³HR system according to a preferred embodiment of the present invention.

With reference now to FIG. 1, the preferred embodiment of the present invention may be described. The P³HR architecture includes provider 10. Provider 10 may be any party that requires access to patient information, including, for example, medical practitioners, pharmacies, medical patients, insurance providers, and other authorized parties. A number of subcomponents are preferably associated with provider 10, as depicted in FIG. 1.

Remote update server 12 is accessible to remote computer systems, as will be described following. Communications with remote update server 12 may be performed over communications network 20. Such network in the preferred embodiment is the Internet, but other networks, telephone communications, or the like may be substituted in alternative embodiments. The architecture further comprises local backup server 18 for storing and retrieving information about medical patients, medical practitioners, pharmacies and insurance providers. Remote update server 12 is operated in conjunction with P³HR manager application 22, as will be described following in connection with FIG. 2, which allows communication with provider 10 and transfers information to and from doctor P³HR 14. Communication over network 20 uses the P³HR authentication protocol suite, as described following, to insure secure communication between provider 10 and the local client computers as may be used to access patient P³HR 24.

Encrypting patient data is a key step in protecting it from unauthorized use. It is also important to back up patient data on a regular basis and store the backup in a secure place. Taking the extra step to back up and store patient data by means of local backup server 18 will ensure that the patient will have access to patient data in case of patient P³HR 24 loss, such as by theft, lost device, hardware failure, software failure, or a computer virus.

Provider 10 provides this backup mechanism for patient P³HR 24 whereby the patient data of patient P³HR 24 is uploaded via network 20 on a regular basis and stored in one or more highly sophisticated data centers at local backup server 17. Online backup has the benefits of being automated/no staff time required to implement; transmission and data storage encryption as will be described following, with backups preferably downloaded via Internet, or next-day air for very large files; easy installation; and relatively low cost.

The flash memory database 26 that provides storage for patient P³HR 24 contains a single database which is the ultimate archive of the associated patient's health records. It also provides storage for P³HR manager application 22, which provides functionality for managing the database and for obtaining data from the local computer systems at which patient P³HR 24 is connected, and presenting data to the local databases. SEG is preferably used for implementation of flash memory database 26, although other devices that provide the necessary storage capacity and encryption capability may be substituted in other embodiments.

Patient P³HR 24 includes data domains which preferably comprise demographic, personal, and emergency information, medications taken, health history, records of treatment, and particularly prescriptions for medicines prescribed by doctors. In the preferred embodiment, the data domains comprise different domains that are accessible only by authorized parties, with different access privileges for different classes of authorized parties. Since current SEG devices have a large capacity—roughly 2 GB of non-volatile memory space—the patient's entire medical history may preferably be stored in patient P³HR 24. This history may include, for example, medical images, video data, and sound or ultrasound data. In addition, it may be noted that P³HR 24 is preferably stored in a generic, non-application specific format so that it can be accessed and manipulated when connected to any provider 10 regardless of the type of proprietary health records system that is implemented by provider 10.

Certificate Authority (CA) 28 is an entity, implemented in the preferred embodiment as another server on network 20, which is core to the PKI (Public Key Infrastructure) scheme. PKI schemes are well known in the art. The purpose of CA 28 in the preferred embodiment of the present invention is to issue digital certificates to use by the provider and patient. It exemplifies a trusted third party. CA 28 issues a Public Key Certificate (PKC), which attests that the public key embed belongs to a particular person, server, organization or any other entity as said in the certificate. In such schemes, the obligation or duty of CA 28 is to verify the credentials of the applicants before issuing the certificate so that the users can trust the information in the CA 28 certificates of a particular entity, without any concerns regarding their authenticity.

The functions of provider P³HR 14 include authenticating the provider to remote update server 12, local backup server 18 through firewall 16, and the patient P³HR 24 using Public Key Infrastructure; communicating with remote update server 12 and local backup server 18; reading medical information from patient P³HR 24; and writing medical reports to the patient associated with patient P³HR 24.

Patient P³HR 24 will include functionality to operate as a client to provider 10, to send and receive data as indicated previously. Patient P³HR 24 also includes on board the capability to perform the functions in a standalone mode, where it is not connected to the server at all and relies solely on the smart card processor associated with flash memory database 26. Patient P³HR 24 acts as an authentication device and authenticates the patient to the system as well as to remote update server 12 if connected.

The P³HR authentication protocol suite, as implemented as P³HR manager application 22, is based on public key cryptography. A patient sends a message to a doctor (or other provider), and the doctor responds with the information needed to authenticate itself. The patient and doctor perform an additional exchange of session keys, and the authentication dialogue ends. When authentication is completed, secure communication can begin between the doctor and the patient using the secret keys established during the authentication process. The doctor always authenticates his identity to the patient. However, the patient might not need to authenticate with the doctor, depending on the application. The authentication method (primarily which digital certificate format will be used) depends on the negotiated cipher suite.

Figure 2:
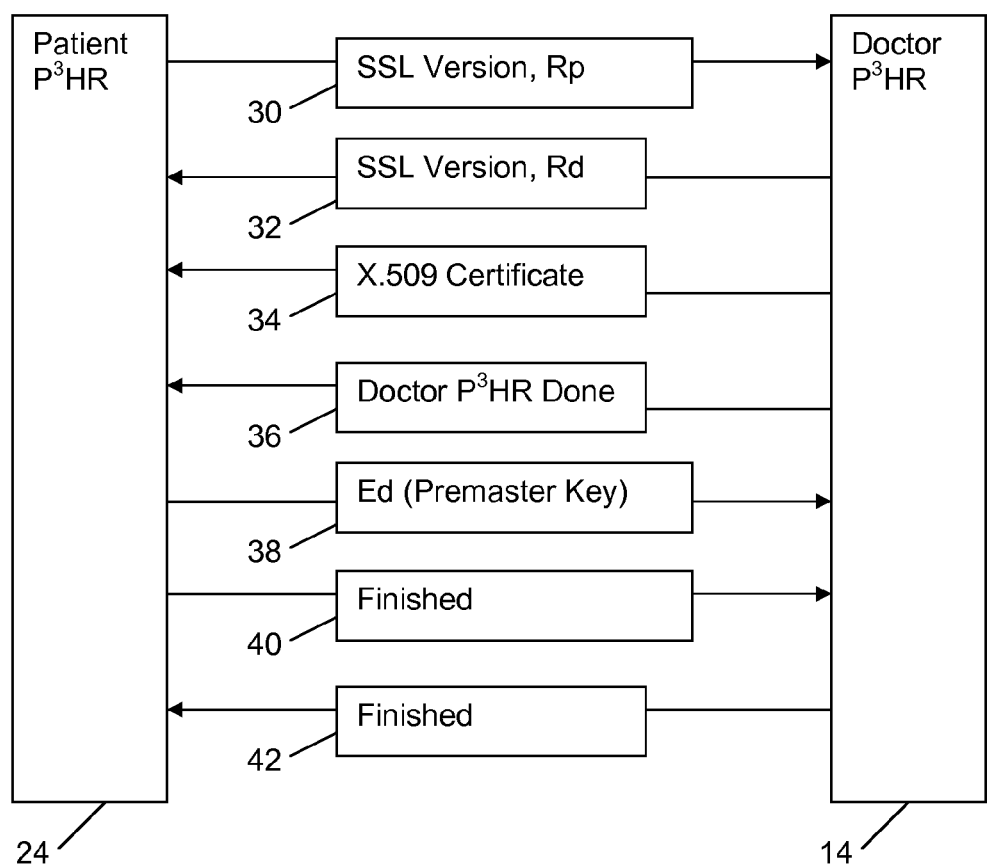
FIG. 2 is a functional schematic of the sequence of events during authentication between a patent P³HR and provider P³HR according to a preferred embodiment of the present invention.

The particular method used in the preferred embodiment of the present invention for authentication and communication is illustrated in FIG. 2. At step 30, the patient at patient P³HR 24 initiates a session by sending a Patient Hello message to the doctor at provider P³HR 14. The Patient Hello message contains a 4-byte number that consists of the patient's date and time, plus a cryptographically-generated pseudorandom number (Rp). This is used in the calculation of the Master Secret from which the encryption keys are derived, as described following.

At step 32, the doctor responds with a Doctor Hello message. The Doctor Hello message includes a 4-byte representation of the doctor's date and time along with a cryptographically-generated pseudorandom number (Rd). This number, along with the Patient Random, is used by both the patient and the doctor to generate the Master Secret from which the encryption keys will be derived.

At step 34, the doctor sends his certificate to the patient. The doctor certificate contains the doctor's public key. The patient uses this key to authenticate the doctor and to encrypt the Premaster Secret. The Doctor Certificate message includes the doctor's certificate list: the first certificate in the list is the doctor's X.509v3 certificate that contains the doctor's public key, although other certificates may be sent as well in various embodiments.

At step 36, the Doctor Hello Done Message indicates that the doctor is finished and awaiting a response from the patient. This message has no content. It signals that the Doctor Hello sequence is finished.

At step 38, the patient sends a Patient Key Exchange message after computing the premaster secret using the two random values that are generated during the Patient Hello message and the Doctor Hello message. Before it is transmitted to the doctor, the premaster secret is encrypted by the public key from the doctor's certificate. Both parties compute the master secret locally and derive the session key from it. If the doctor can decrypt this data and complete the protocol, the patient is assured that the doctor has the correct private key. This step is important to prove the authenticity of the doctor. Only the doctor with the private key that matches the public key in the certificate can decrypt this data and continue the protocol negotiation.

The Patient Key Exchange message includes the premaster secret. This is the patient-generated number (48-byte using, preferably, the well-known RSA algorithm), encrypted with the doctor's public key, that is used with the Patient Random and the Doctor Random to create the Master Secret. The Master Secret results from the pseudorandom material that is exchanged in the Patient Hello message and Doctor Hello message. Both the doctor and the patient create the Master Secret key. It is never exchanged. To create the Master Secret key, the system passes the following as variables to a pseudorandom function (PRF): (1) the 48-byte premaster secret; (2) the literal phrase "P³HR secret"; and (3) the concatenation of Patient Random number and Doctor Random number. The result is the Master Secret.

At step 40, the finished message is a hash of the entire conversation which provides further authentication of the patient. This message is a complicated verification that the patient who is sending the finished message is truly the patient who started the Hello conversation.

If the doctor has a copy of the private half of its public key pair, it can decrypt this message and generate a matching set of encryption keys. The doctor responds to the patient at step 42 with a request to communicate with secret key cryptography, so that both parties have acknowledged that they will use the cryptography and keys that they have agreed upon.

So far in this process, patient P³HR 24 and provider P³HR 14 have been authenticated through the use of certificates and public/private keys, a premaster secret and other data have been exchanged to create the master secret, and both the doctor and the patient have successfully proven that they have not changed identities throughout the Hello sequence. Now patient P³HR 24 and provider P³HR 14 can begin to communicate, using the established keys and parameters.

In the preferred embodiment, patient P³HR 24 enables fingerprint match-on-card user authentication as an alternative or complement to smart card personal identification number (PIN) verification. This in turn gives access to the digital certificates on the card. Traditionally, smart cards are protected by a PIN that the user must present to access the cryptographic keys and associated digital certificates stored inside the card. Patient P³HR 24 extends PIN-based authentication with a flexible system that can be deployed to use fingerprint authentication instead of the smart card PIN. This provides user convenience and cost savings as users do not need to remember the value of the PIN, and are less likely to call the designated helpdesk for forgotten password/PIN support in the case of emergency. Fingerprint readers and associated software to provide this functionality are well known in the art.

Patient P³HR 24 preferably offers three different user authentication modes in order to optimize security and convenience based on the specific requirements and security policies: (1) PIN only, which is the traditional mode of authentication; (2) Fingerprint only, conveniently replacing the use of a PIN; or (3) PIN or Fingerprint, as options providing higher convenience by giving the user two different authentication options.

The preferred embodiment of the present invention thus presents a novel architecture, Privacy Preserving Portable Health Record (P³HR), based on Smart Enterprise Guardian (SEG) or similar technologies that incorporate smart card security and advanced flash storage encryption technology. The P³HR gives a patient the flexibility of using the services of a variety of generally unrelated healthcare practitioners and other providers with control over their health records. The salient features of the P³HR system include: strong multifactor authentication using biometrics, public key infrastructure to verify the credentials of the applicants, an authentication protocol suite for authorization and secure online updates, and local backup to store patient data which ensures that the patient will have continuous access to data in the case of P³HR theft, lost device, or other failures.

As used herein, "comprising" is synonymous with "including," "containing," or "characterized by," and is inclusive or open-ended and does not exclude additional, unrecited elements or method steps. As used herein, "consisting of" excludes any element, step, or ingredients not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Thus, additional embodiments are within the scope of the invention and within the following claims.

In general the terms and phrases used herein have their art-recognized meaning, which can be found by reference to standard texts, journal references and contexts known to those skilled in the art. The preceding definitions are provided to clarify their specific use in the context of the invention.

All patents and publications mentioned in the specification are indicative of the levels of skill of those skilled in the art to which the invention pertains. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention as set forth in the appended claims.

The invention claimed is:

1. A portable health record system, comprising:
   a. an update server configured to provide secure access to a plurality of provider health records each stored on one of a plurality of remote computers, wherein each of the plurality of provider health records comprises health-related data regarding a patient;
   b. a client server in communication with the update server and the plurality of remote computers via a network;
   c. a portable smart card in selectively disengageable communication with the client server, wherein the smart card comprises
      i. non-volatile memory comprising a patient health record comprising health-related data regarding the patient wherein the patient health record comprises a generic, non-application specific format; and
      ii. a portable health record manager application operable in a standalone mode when not connected to the client server or update server to provide access to the patient health record that is stored in the non-volatile memory without using software stored on the client server, and when connected to the client server to communicate with the update server over the network to securely update health-related data regarding the patient on the patient health record from at least one of the plurality of provider health records; and
   d. a backup server in communication with the update server and the client server and operable to store a backup copy of the patient health record.

2. The system of claim 1, further comprising a certificate authority operable to authenticate the provider and patient to each other for the transfer of data between the provider health record and the patient health record.

3. The system of claim 2, wherein the certificate authority is operable to generate a public key certificate.

4. The system of claim 2, wherein the patient health record data comprises one or more of patient demographic information, patient personal information, patient emergency contact information, patient prescription medications, patient health history, or patient medical treatment records.

5. The system of claim 4, wherein each of the plurality of provider health records comprises a subset of the health-related data of the patient health record.

6. The system of claim 2, wherein the smart card is an SEG device.

7. The system of claim 2, wherein the smart card comprises a non-volatile memory space of at least 2 GB.

8. The system of claim 2, further comprising a biometric reading device, and wherein the portable health record manager application is operable to receive a biometric reading for purposes of authenticating the patient.

9. The system of claim 8, wherein the biometric reading device is a fingerprint scanner.

10. The system of claim 9, wherein the portable health record manager application is further operable to receive a personal identification number (PIN) for purposes of authenticating the patient.

11. A method of authenticating a provider and patient using a portable health record system, the method comprising the steps of:
    a. sending a patient hello message over a network from the patient, at a client server in selectively disengageable communication with a portable smart card comprising non-volatile memory storing a patient health record and operable in a standalone mode when not connected to the client server or a remote update server to provide access to the patient health record that is stored in the non-volatile memory without using software stored on the client server, and, when connected to the client server, to provide via the remote update server access to a provider health record stored at the provider, wherein the patient hello message comprises a pseudorandom number;

b. sending a provider hello message over the network from the provider to the patient via the remote update server, wherein the provider hello message comprises a pseudorandom number;

c. computing at a portable health record manager application operating on the client computer and stored on the smart card a premaster secret using the patient hello message pseudorandom number and the provider hello message pseudorandom number;

d. sending a patient key exchange message from the patient to the provider via the remote update server, wherein the patient key exchange message comprises the premaster secret;

e. computing a master secret at the provider utilizing the pre-master secret;

f. sending, via the remote update server, a patient finish message from the patient to the provider comprising a hash of the previous messages exchanged by the provider and patient;

g. sending a provider finish message from the provider to the patient; and h. sending at least one encrypted message between the provider and patient, wherein the encrypted message may be decrypted using the master secret.

12. The method of claim 11, wherein the provider hello message further comprises a provider certificate, which comprises a public key.

13. The method of claim 12, further comprising the step of encrypting the premaster secret using the public key from the provider certificate prior to sending the patient key exchange message.

14. The method of claim 12, wherein the provider hello message comprises a plurality of provider certificates.

15. The method of claim 11, wherein the step of computing a master secret utilizing the pre-master secret is performed at both the patient and the provider.

16. The method of claim 15, wherein the step of computing a master secret further comprises the input of a concatenation of the patient pseudorandom number and the provider pseudorandom number.

17. The method of claim 16, wherein the step of computing a master secret further comprises the input of a text phrase.

18. The method of claim 11, wherein the provider finish message comprises a request to communicate with secret key cryptography.

19. The method of claim 11, wherein the patient hello message and provider hello message each further comprise a number representing a local date and time.

20. The method of claim 11, wherein the premaster secret comprises a length of at least 48 bytes.

* * * * *